United States Patent
Anderson

(10) Patent No.: US 9,170,238 B2
(45) Date of Patent: Oct. 27, 2015

(54) ACOUSTIC FLUID VALVE CALIBRATION

(71) Applicant: FISHER CONTROLS INTERNATIONAL LLC, Marshalltown, IA (US)

(72) Inventor: Shawn William Anderson, Haverhill, IA (US)

(73) Assignee: FISHER CONTROLS INTERNATIONAL LLC, Marshalltown, IA (US)

( * ) Notice: Subject to any disclaimer, the term of this patent is extended or adjusted under 35 U.S.C. 154(b) by 343 days.

(21) Appl. No.: 13/734,480

(22) Filed: Jan. 4, 2013

(65) Prior Publication Data

US 2014/0190263 A1 Jul. 10, 2014

(51) Int. Cl.
*G01N 29/14* (2006.01)
*F16K 37/00* (2006.01)

(52) U.S. Cl.
CPC ............ *G01N 29/14* (2013.01); *F16K 37/0075* (2013.01); *F16K 37/0091* (2013.01)

(58) Field of Classification Search
CPC .. G01N 29/14; F16K 37/0075; F16K 37/0091
USPC ......................................................... 73/587
See application file for complete search history.

(56) References Cited

U.S. PATENT DOCUMENTS

| | | | |
|---|---|---|---|
| 4,260,132 A | 4/1981 | Habiger | |
| 5,008,841 A | 4/1991 | McElroy | |
| 5,152,308 A | 10/1992 | Koch | |
| 5,433,245 A * | 7/1995 | Prather et al. | 137/554 |
| 5,691,478 A * | 11/1997 | Barry et al. | 73/721 |
| 5,715,866 A * | 2/1998 | Granger | 137/624.11 |
| 6,128,946 A | 10/2000 | Leon et al. | |
| 6,131,609 A * | 10/2000 | Metso et al. | 137/552 |
| 6,134,949 A | 10/2000 | Leon et al. | |
| 7,509,975 B2 * | 3/2009 | Hodge et al. | 137/456 |
| 7,940,189 B2 | 5/2011 | Brown | |
| 7,950,623 B2 | 5/2011 | Sasaki et al. | |
| 2005/0126639 A1* | 6/2005 | Ens et al. | 137/554 |
| 2008/0092632 A1* | 4/2008 | Hoffmann et al. | 73/40.5 A |
| 2014/0067135 A1 | 3/2014 | Lehnert et al. | |

FOREIGN PATENT DOCUMENTS

| | | |
|---|---|---|
| JP | H0245069 B2 * | 10/1990 |
| KR | 100888320 B1 * | 3/2009 |
| WO | 2012139236 | 10/2012 |

OTHER PUBLICATIONS

International Searching Authority, "Written Opinion of the International Searching Authority," issued in connection with PCT application PCT/US2014/010044, on Apr. 17, 2014, 4 pages.

(Continued)

*Primary Examiner* — J M Saint Surin
(74) *Attorney, Agent, or Firm* — Hanley, Flight and Zimmerman, LLC

(57) ABSTRACT

Methods and apparatus for acoustic fluid valve calibration are disclosed herein. An example method involves rotating a closure member of a valve to a involves rotating a closure member of a valve to a plurality of positions along a valve stroke, obtaining acoustic emission signals generated by a fluid passing through the valve using a sensor when the closure member is in the positions, and identifying, using a processor, a zero position of the closure member based on the acoustic emission signals.

19 Claims, 2 Drawing Sheets

(56) References Cited

OTHER PUBLICATIONS

International Searching Authority, "International Search Report," issued in connection with PCT application PCT/US2014/010044, on Apr. 17, 2014, 2 pages.

International Bureau, "International Preliminary Report on Patentability," issued in connection with application No. PCT/US2014/010044, mailed on Jul. 16, 2015, 6 pages.

* cited by examiner

ACOUSTIC FLUID VALVE CALIBRATION

FIELD OF THE DISCLOSURE

The disclosure relates generally to process industry control valves and, more particularly, to acoustic fluid valve calibration.

BACKGROUND

Fluid control valves, such as ball valves, typically include a closure member that may be rotated to an open or closed position with respect to a valve seal to permit or restrict the passage of fluid flow through the valve. A fluid control valve that does not have a properly positioned closure member in the closed position can leak process fluid, thereby resulting in an ineffective sealing of the valve.

SUMMARY

Methods and apparatus for acoustic fluid valve calibration are disclosed. An example method involves rotating a closure member of a valve to a plurality of positions along a valve stroke, obtaining acoustic emission signals generated by a fluid passing through the valve using a sensor when the closure member is in the positions, and identifying, using a processor, a zero position of the closure member based on the acoustic emission signals.

An example apparatus includes a rotary control valve having a closure member, a sensor for obtaining acoustic emission signals generated by fluid passing through the valve, and a processor to determine a zero position of the closure member based on the acoustic emission signals.

Another example apparatus includes means for obtaining acoustic emission signals generated by a fluid when a closure member of a valve is in a plurality of positions along a valve stroke, and means for identifying a zero position of the closure member based on the acoustic emission signals.

DETAILED DESCRIPTION

Figure 1:
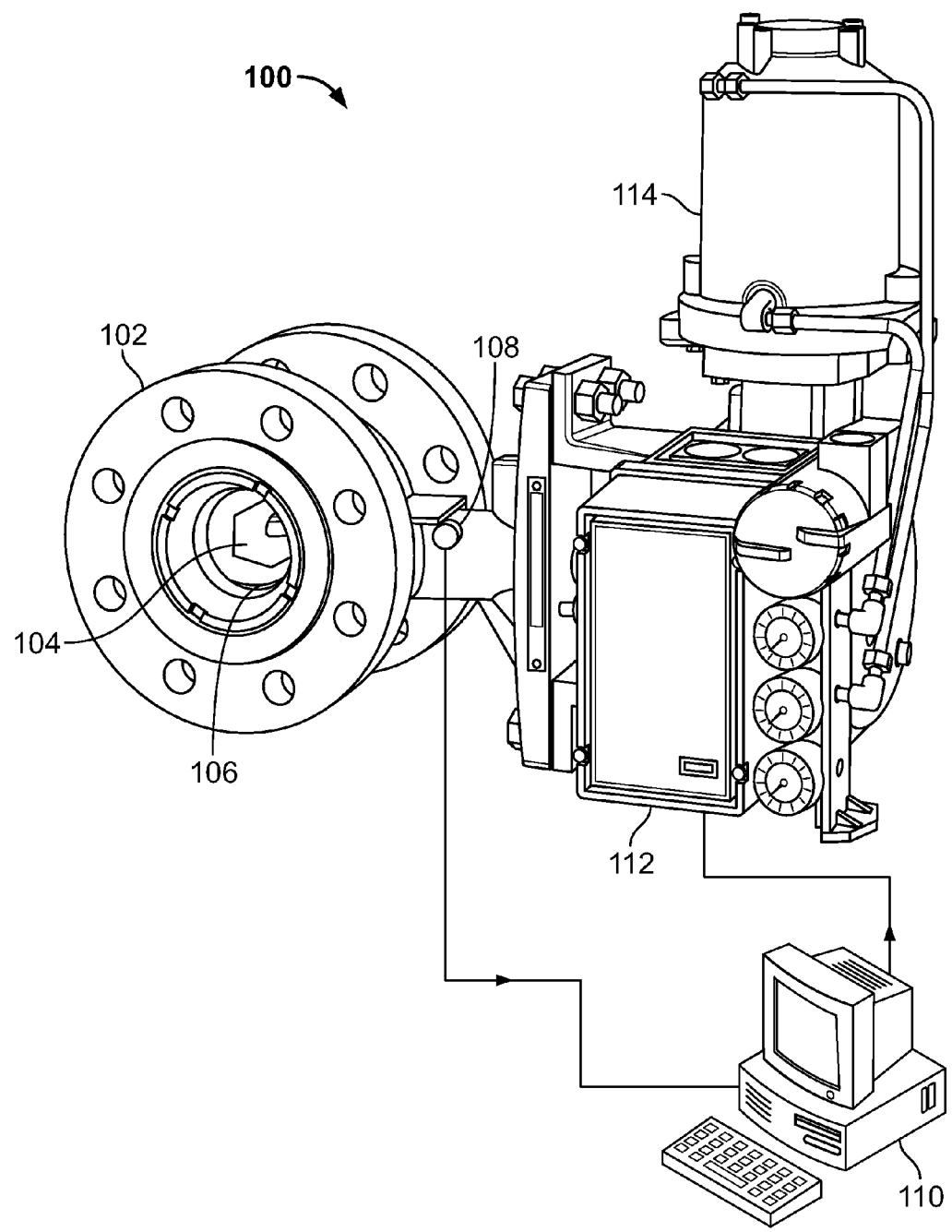
FIG. 1 is an example apparatus to identify a zero position of a closure member of a fluid control valve according to one or more aspects of the present disclosure.

The example methods and apparatus described herein relate to acoustic calibration of fluid control valves. More specifically, the examples described herein may be used to identify an optimal zero or center position (e.g., a minimal leakage or flow position) of a closure member of a fluid control valve. In particular, the examples described herein may use acoustic emission signals emitted as a result of fluid flowing through a valve to enable positioning of a closure member of the valve at an optimal zero or center position during operation and, as a result, achieve minimal or substantially zero leakage through the valve in the closed position.

Fluid control valves generally include an internal component known as a closure member or trim that is positioned with respect to a valve seal to control the flow of fluid through the valve. In a rotary valve, a closure member may be rotated about an axis along a path that may be referred to as a valve stroke. When a closure member is in a fully closed position with respect to the valve seal, fluid is substantially prevented from passing through the valve. This fully closed position may correspond to a mechanical stop of the valve. Rotating the closure member a distance along the valve stroke of, for example, approximately 90 degrees from the fully closed position allows fluid to flow through the valve with minimal restriction. In such a position, the closure member may be considered to be in a fully open position. As the closure member is rotated about its axis to different positions along the valve stroke toward or away from the fully closed position, where the different positions may be located between the fully open and fully closed positions, the flow of fluid through the valve is restricted accordingly.

In some examples of the methods and apparatus described herein, as the closure member of the valve is rotated to different positions along the valve stroke during operation, a sensor may detect corresponding acoustic energy or emission signals generated by turbulent fluid flow at the different positions. As described in more detail below, analysis of these acoustic emission signals enables identification of the optimal zero or center position of the closure member, which may be used to position the closure member relative to a valve seal for minimal or substantially zero flow or leakage through the valve. This optimal zero or center position may correspond to a stroke position of the valve that is spaced away from the fully closed or the mechanical stop position of the valve. In one example, the optimal zero or center position for a valve corresponds to a stroke position at which fluid turbulence and, thus, the energy associated with the acoustic emissions due to such turbulence, are minimized.

While some known technologies detect acoustic emissions to generally quantify leakage through valves, such technologies are not used to identify an optimal zero or center position of a valve closure member relative to a valve seal as described in connection with the examples herein.

In accordance with the teachings disclosed herein, a sensor may be positioned proximate to a fluid control valve. As the closure member is rotated to different positions along the valve stroke, the sensor detects acoustic emission signals generated by the turbulent flow of fluid through the valve at the different positions including, for example, a first position and a second position different from the first position. A processor or any other suitable processing device may determine the optimal zero or center position of the closure member based on analysis of the acoustic emission signals collected at the first and second positions. Moving the closure member to the zero position may be accomplished by, for example, an actuator and a digital valve positioner.

The example methods and apparatus described herein may be implemented when the valve is installed and operating in a process application, thus providing for identification and positioning of the closure member at the zero position while the valve is in use. Additionally or alternatively, the disclosed methods and apparatus may be used to identify the optimal zero or center position of the valve during the manufacture of the valve. In further examples, the examples provided herein may be part of a plant control system or asset management software package. Other uses of the disclosed methods and apparatus include, but are not limited to, detecting valve seal or closure member damage and/or avoiding over-rotation of the closure member.

FIG. 1 depicts an example apparatus 100 for identifying the optimal zero or center position of a fluid control valve 102 having a closure member 104. The fluid control valve 102 may be a rotary control valve, such as a ball valve, a butterfly valve, or any other type of fluid control valve. The fluid control valve 102 may be a position-seated valve, a torque-seated valve, or any other arrangement. The fluid control valve 102 further includes a valve seal 106 and a sensor 108. The sensor 108 may be positioned proximate to the fluid control valve 102 and, in some examples, is proximate or adjacent to the valve seal 106. The sensor 108 may be, for example, a piezoceramic sensor. In further examples, multiple sensors may be positioned at multiple locations proximate to the fluid control valve 102 and/or the valve seal 106.

In operation, acoustic emission signals generated by fluid passing through the fluid control valve 102 as the closure member 104 is rotated are detected by the sensor 108 and recorded and analyzed by a processor 110. The analysis of the acoustic emission signals performed by the processor 110 may involve, for example, calculating a root mean square. In some examples, other energy parameters may be measured and/or calculated by the sensor 108 and the processor 110 including, but not limited to, airborne noise, ultrasonic signals, or hit amplitudes of signals generated by noise other than from passing fluid and detected by the sensor 108, such as noise resulting from the movement of the valve itself. The processor 110 may analyze the acoustic emission signals detected by the sensor 108 and associate the acoustic emission signals with positions of the closure member 104 to determine an optimal zero or center position of the closure member 104. Upon identification of the optimal zero or center position, the processor 110 may communicate with a digital valve positioner 112 and an actuator 114 to position the closure member 104 at the zero position.

In one example method for identifying the optimal zero or center position of fluid control valve 102, the closure member 104 may be rotated to a plurality of positions along the valve stroke. In such an example, acoustic emission signal data is collected by the sensor 108 for all of the positions along the valve stroke. The processor 110 may identify a valve closure member position corresponding to a minimal acoustic emission signal detected by the sensor 108 at the plurality of positions. In some examples, the processor may identify the positions corresponding to minimal acoustic emission signals and perform a midpoint calculation using signal data from adjacent positions to identify the zero position. In further examples, acoustic emission signals are collected continuously as the closure member 104 is rotated toward the center position, and rotated beyond the center position. In such examples, the processor 110 identifies a valve closure member position corresponding to a minimal acoustic emission signal detected by the sensor 108.

Figure 2:
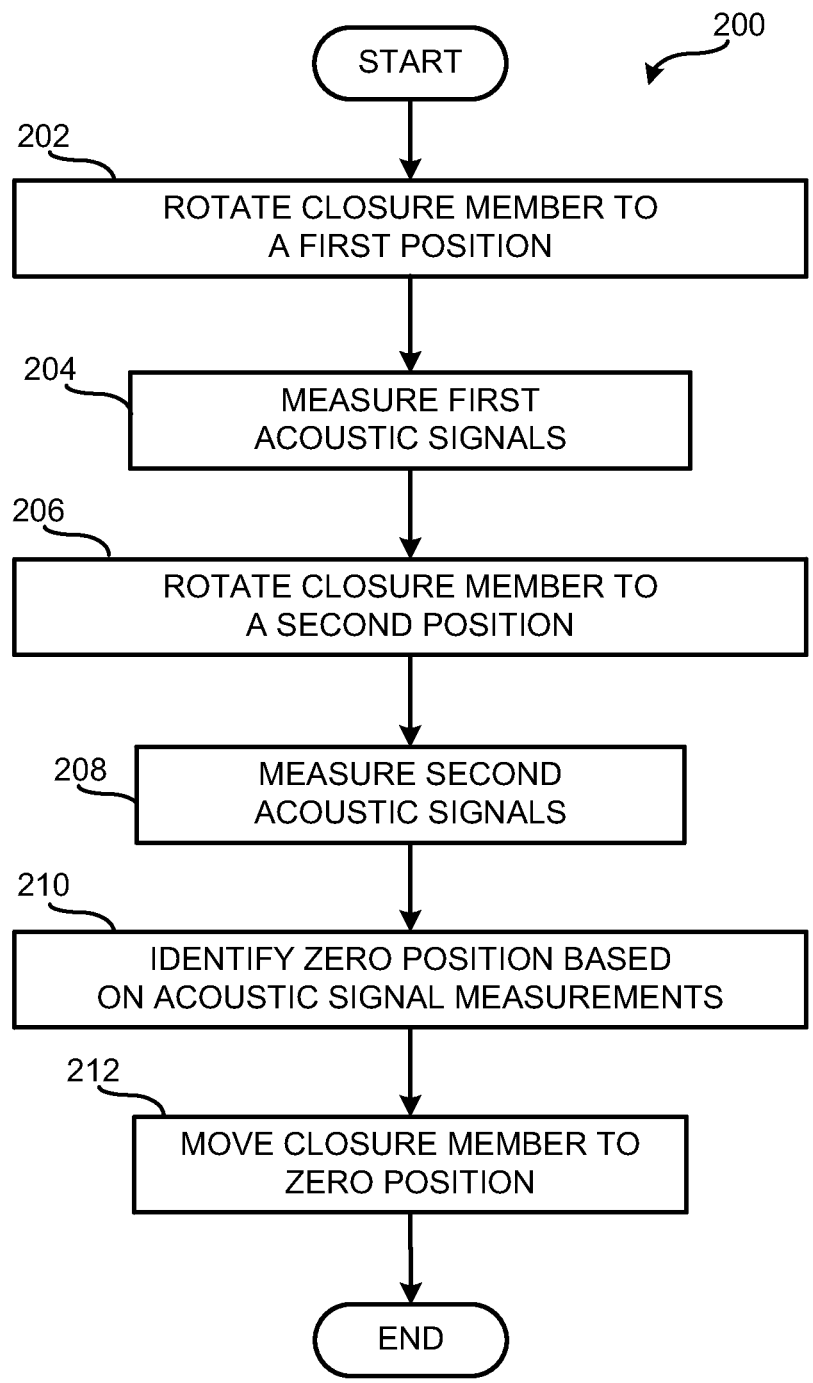
FIG. 2 is a flow diagram of an example method that can be used to implement the examples described herein.

FIG. 2 depicts an example flow diagram representative of a method 200 that may be implemented to identify the optimal zero or center position of a fluid control valve. The example method 200 of FIG. 2 may be performed using a processor, a controller and/or any other suitable processing device. For example, the example method 200 of FIG. 2 may be implemented using coded instructions (e.g., computer readable instructions) stored on a tangible computer readable medium such as a flash memory, a read-only memory (ROM), and/or a random-access memory (RAM). As used herein, the term tangible computer readable medium is expressly defined to include any type of computer readable storage and to exclude propagating signals. Additionally or alternatively, the example method 200 of FIG. 2 may be implemented using coded instructions (e.g., computer readable instructions) stored on a non-transitory computer readable medium such as a flash memory, a read-only memory (ROM), a random-access memory (RAM), a cache, or any other storage media in which information is stored for any duration (e.g., for extended time periods, permanently, brief instances, for temporarily buffering, and/or for caching of the information). As used herein, the term non-transitory computer readable medium is expressly defined to include any type of computer readable medium and to exclude propagating signals.

Further, although the example method 200 of FIG. 2 is described with reference to the flow diagram of FIG. 2, other methods of implementing the example method 200 of FIG. 2 may be employed. For example, the order of execution of the blocks may be changed, and/or some of the blocks described may be changed, eliminated, sub-divided, or combined. Additionally, any or all of the example operations of FIG. 2 may be performed sequentially and/or in parallel by, for example, separate processing threads, processors, devices, etc.

The example method 200 of FIG. 2 may be used to identify the optimal zero or center position of the closure member 104 of the fluid control valve 102. The example method 200 may be initiated by a command to rotate the closure member 104 to a first position (block 202). In one example, the closure member 104 may be rotated to a first position along the valve stroke. For example, in the first position, the closure member 104 may be located between a fully open position and a fully closed position and fluid may pass through fluid control valve 104. The sensor 108 then measures acoustic emission signals when the closure member 104 is in this first position (block 204). The closure member may be rotated to a plurality of positions along the valve stroke; as such, the example method 200 is not limited to rotating the closure member to only one first position. The closure member 104 may be then rotated to a second position (block 206) and the sensor 108 measures acoustic emission signals when the closure member 104 is in this second position (block 208). In one example, the second position may be located at a position beyond the optimal zero or center position of the valve (e.g., between a fully closed position and the center position). In this example, the closure member 104 has been rotated along the valve stroke from the first position, reached the center position, and rotated beyond the center position toward the fully closed (e.g., mechanically stopped) position. In further examples, the second position corresponds to a position wherein sensor 108 detects increased second acoustic emission signals relative to the first acoustic emission signals. The closure member 104 may be rotated to a plurality of positions along the valve stroke; as such, the example method 200 is not limited to rotating the closure member 104 to only one second position.

The acoustic emission signals collected at the first and second positions by sensor 108 are analyzed by a suitable processing device, such as the processor 110. The processor 110 may calculate, for example, the root mean square noise levels of the acoustic emission signals recorded by the sensor 108 and identify the optimal zero or center position of the closure member 104 based on analysis of the acoustic emission signal data (block 210). For example, the processing device may identify a valve closure member position corresponding to a minimal acoustic emission signal detected by the sensor 108 between the first and second positions and associate this position with the optimal zero or center position of the closure member 104.

In another example, the processing device may determine a position midway between the first position and second position corresponding to increased first and second acoustic emission signals as detected by the sensor 108. The processor 110 may associate the midway position with the optimal center or zero position of the closure member 104. Such a midway position may be determined by various signal analysis calculations. For example, in the event the measurement of the second acoustic emission signal detected by the sensor 108 is substantially equal to the measurement of the first acoustic emission signal, a midpoint calculation may be performed by the processor 110 to determine a position midway between the positions corresponding to the first and second acoustic emission signals. Alternatively, in some examples, the first acoustic emission signal and second acoustic emission signal may correspond to substantially different noise levels generated by the passing fluid. In such examples, a curve fitting of, for example, a polynomial curve generated by acoustic emission signal data detected by the sensor 108 may be performed by the processor 110 to determine the optimal zero or center position. Such a curve fitting using, for example, a second order function, may associate the acoustic emission signal measurements with the positions of closure member 104 to identify the optimal zero or center position of closure member 104 corresponding to a minimal acoustic emission signal detected by the sensor 108.

Alternatively, the described method may be performed manually by an individual using a suitable handheld device for processing acoustic emission signals. In the event that the zero or center position has been identified, the example method 200 may involve moving the closure member to the zero position using, for example, the digital valve positioner 112 and the actuator 114.

Although the foregoing detailed description references various specific examples, it is to be understood that modifications and alterations in the structure and arrangement of those examples other than those specifically set forth herein may be achieved by those skilled in the art and that such modifications and alterations are to be considered as within the overall scope of this disclosure.

What is claimed is:

1. A method, comprising:
rotating a closure member of a valve to a plurality of positions along a valve stroke;
obtaining acoustic emission signals generated by a fluid passing through the valve using a sensor when the closure member is in the positions;
identifying a minimal acoustic emission signal from the acoustic emission signals; and
determining, using a processor, a zero position of the closure member based on the minimal acoustic emission signal.

2. The method of claim 1, wherein the plurality of positions comprises a first position in which the closure member is between a fully open position and a fully closed position of the valve, and a second position in which the closure member is located beyond the zero position.

3. The method of claim 2, wherein identifying the minimal acoustic emission signal comprises detecting the minimal acoustic emission signal between the first position and the second position.

4. The method of claim 3, wherein determining the zero position further comprises calculating a position between the first position and the second position based on the identification of the minimal acoustic emission signal.

5. An apparatus, comprising:
a rotary control valve having a closure member;
a sensor for obtaining acoustic emission signals generated by fluid passing through the valve; and
a processor to:
identify a minimal acoustic emission signal from the acoustic emission signals; and
determine a zero position of the closure member based on the minimal acoustic emission signal.

6. The apparatus of claim 5, wherein the sensor is positioned proximate to a seal of the valve.

7. The apparatus of claim 5, wherein the sensor is a piezoceramic sensor.

8. The apparatus of claim 5, wherein the closure member is rotated to a first position and a second position.

9. The apparatus of claim 8, wherein the sensor is to obtain first acoustic emission signals when the closure member is rotated to the first position and second acoustic emission signals when the closure member is rotated to the second position.

10. The apparatus of claim 9, wherein the processor is to identify the minimal acoustic signal based on the first and second acoustic emission signals obtained at the first position and the second position.

11. The apparatus of claim 5 further comprising a digital valve positioner for moving the closure member to the zero position.

12. The apparatus of claim 5, wherein the rotary control valve is position-seated or torque-seated.

13. The apparatus of claim 5, wherein the processor is to calculate a root mean square of the acoustic emission signals and identify the minimal acoustic emission signal based on the calculation.

14. The apparatus of claim 5, wherein the acoustic emission signals comprise ultrasonic signals.

15. The apparatus of claim 5, wherein the acoustic emission signals comprise airborne noise.

16. An apparatus, comprising:
means for obtaining acoustic emission signals generated by a fluid when a closure member of a valve is in a plurality of positions along a valve stroke; and
means for determining a zero position of the closure member based on a minimal acoustic emission signal in the acoustic emission signals, the means for determining the zero position including means for identifying the minimal acoustic emission signal.

17. The apparatus of claim 16, wherein the means for obtaining the acoustic emission signals is a piezoceramic sensor.

18. The apparatus of claim 16, wherein the means for determining the zero position is a processor.

19. The apparatus of claim 16, further comprising means for moving the closure member to the zero position.

* * * * *